United States Patent
Simhadri et al.

(10) Patent No.: US 9,487,487 B2
(45) Date of Patent: Nov. 8, 2016

(54) PROCESS FOR PREPARATION OF MONTELUKAST SODIUM

(71) Applicant: Laurus Labs Private Ltd. Plot No. DS1, Hyderabad (IN)

(72) Inventors: Srinivas Simhadri, Hyderabad (IN); Yaseen Mohammad, Hyderabad (IN); Venkata S. Indukuri, Hyderabad (IN); Seeta R. Gorantla, Hyderabad (IN); Satyanarayana Chava, Hyderabad (IN)

(73) Assignee: LAURUS LABS PRIVATE LIMITED, Hyderabad (IN)

( * ) Notice: Subject to any disclaimer, the term of this patent is extended or adjusted under 35 U.S.C. 154(b) by 0 days.

(21) Appl. No.: 14/395,368

(22) PCT Filed: May 17, 2013

(86) PCT No.: PCT/IB2013/000973
§ 371 (c)(1),
(2) Date: Oct. 17, 2014

(87) PCT Pub. No.: WO2014/001860
PCT Pub. Date: Jan. 3, 2014

(65) Prior Publication Data
US 2015/0299127 A1    Oct. 22, 2015

(30) Foreign Application Priority Data

May 18, 2012  (IN) ............. 1977/CHE/2012
Nov. 7, 2012  (IN) ............. 4664/CHE/2012

(51) Int. Cl.
*C07D 215/18*    (2006.01)
(52) U.S. Cl.
CPC .................. *C07D 215/18* (2013.01)

(58) Field of Classification Search
None
See application file for complete search history.

(56) References Cited

U.S. PATENT DOCUMENTS

| 5,614,632 | A  | * | 3/1997  | Bhupathy et al. | ............ 546/180 |
| 2009/0281323 | A1 | * | 11/2009 | Chawla et al.   | ............... 546/174 |
| 2011/0092708 | A1 | * | 4/2011  | Gorantla et al. | .............. 546/174 |

FOREIGN PATENT DOCUMENTS

| WO | 2006008751       | 1/2006  |
| WO | WO-2006/008751 A2 | 1/2006  |
| WO | 2006058545       | 6/2006  |
| WO | WO-2006/058545 A1 | 6/2006  |
| WO | 2007116240       | 10/2007 |
| WO | WO-2007/116240 A1 | 10/2007 |

OTHER PUBLICATIONS

International Search Report dated Oct. 17, 2013; International Application No. PCT/IB2013/000973; International Filing Date: May 17, 2013; 4 pages.
Written Opinion dated Oct. 17, 2013; International Application No. PCT/IB2013/000973; International Filing Date: May 17, 2013; 5 pages.

* cited by examiner

*Primary Examiner* — Timothy R Rozof
(74) *Attorney, Agent, or Firm* — Blank Rome, LLP

(57) ABSTRACT

Disclosed is a process for the preparation of montelukast sodium. The process comprises a) reacting 2-(2-(3(S)-(3-(2-(7-chloro-2-quinolinyl)-ethenyl)phenyl)-3-hydroxypropyl) phenyl)-2-propanol with methane sulfonyl chloride and coupling the resultant mesylate compound with 1-(mercaptomethyl)cyclopropane acetic acid in presence of a base and free alkali source followed by saltification with an amine in a single step reaction and b) converting the montelukast amine salt to montelukast sodium salt.

19 Claims, 1 Drawing Sheet

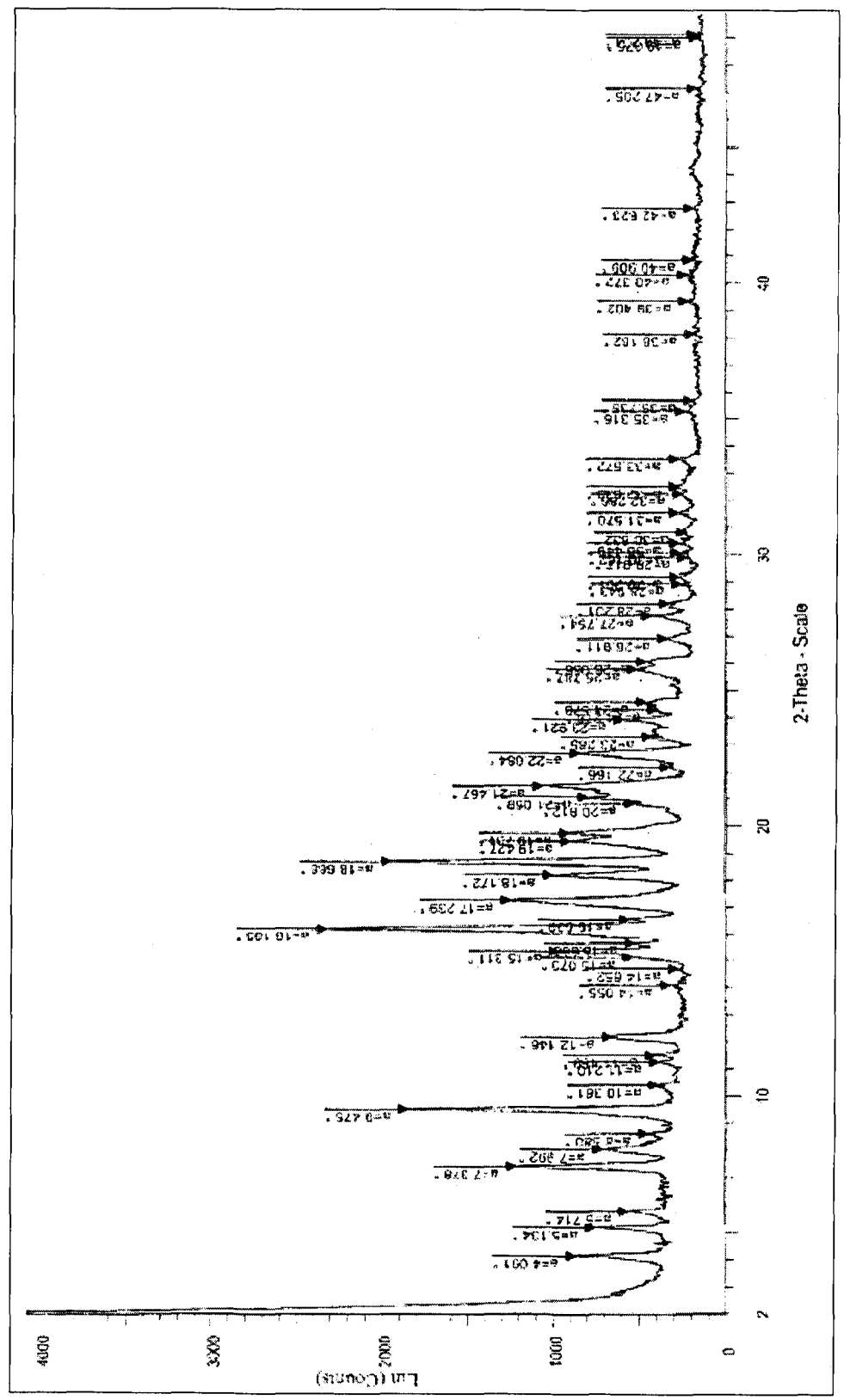

PROCESS FOR PREPARATION OF MONTELUKAST SODIUM

PRIORITY

This application claims the benefit under Indian Provisional Application No. 1977/CHE/2012, filed on May 18, 2012 entitled "Process for preparation of Montelukast and salts thereof", and 4664/CHE/2012, filed on Nov. 7, 2012 entitled "An improved process for preparation of Montelukast Sodium", the contents of each of which are incorporated by reference herein.

FIELD OF THE INVENTION

The present invention generally relates to an improved process for preparing montelukast and salts thereof, particularly montelukast sodium and pharmaceutical compositions containing the same.

BACKGROUND OF THE INVENTION

Montelukast sodium, also known as R-(E))-1-(((1-(3-(2-(7-chloro-2-quinolinyl)ethenyl)phenyl)-3-(2-(1-hydroxy-1-methylethyl)phenyl)propyl)thio)methyl)cyclopropaneacetic acid sodium salt, is represented by the structural Formula I:

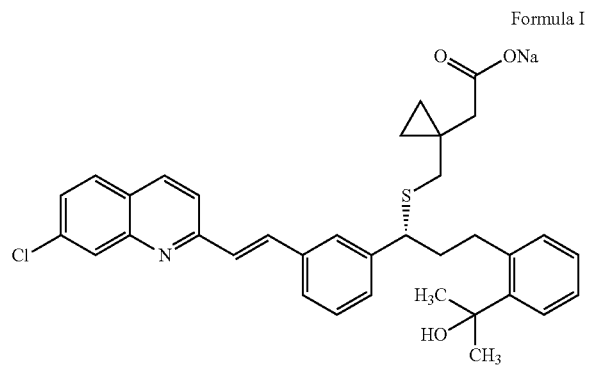

Formula I

Montelukast sodium is a leukotriene antagonist and inhibits the synthesis of leukotriene biosynthesis. It is useful as an antiasthmatic, anti-allergic, anti-inflammatory and cytoprotective agent and hence useful in the treatment of angina, cerebral spasm, glomerular nephritis, hepatic, end toxemia, uveitis and allograft rejection. Montelukast sodium is currently indicated for the treatment of asthma and allergic rhinitis.

Montelukast sodium, formulated as 10.4 mg montelukast sodium tablets, 4.2 or 5.2 mg montelukast sodium chewable tablets or 4.2 mg montelukast sodium oral granules packet, is typically given once daily to the patients for the treatment of asthma and seasonal allergic rhinitis. Montelukast sodium is marketed in the United States and other countries by Merck & Co., Inc. under the trade name Singulair®.

EP Patent No. 0480717 ("the '717 patent") discloses montelukast sodium along with other related compounds and the methods for their preparation. The reported method of synthesis proceeds through corresponding methyl ester namely, and involves coupling methyl 1-(mercaptomethly) cyclopropane acetate with a tetrahydropyran (THP) protected mesylate compound. The methyl ester and the THP group are hydrolyzed to free acid and the later converted directly to montelukast sodium salt. The process is not suitable for large-scale production because it involves multiple steps such as series of protection and deprotection of intermediates and requires tedious chromatographic purification of the methyl ester intermediate and of the final product, which in turn result to an increase in the manufacturing cycle time and a decrease in the product yield. The process disclosed in the '717 patent is schematically represented as follows:

Scheme 1

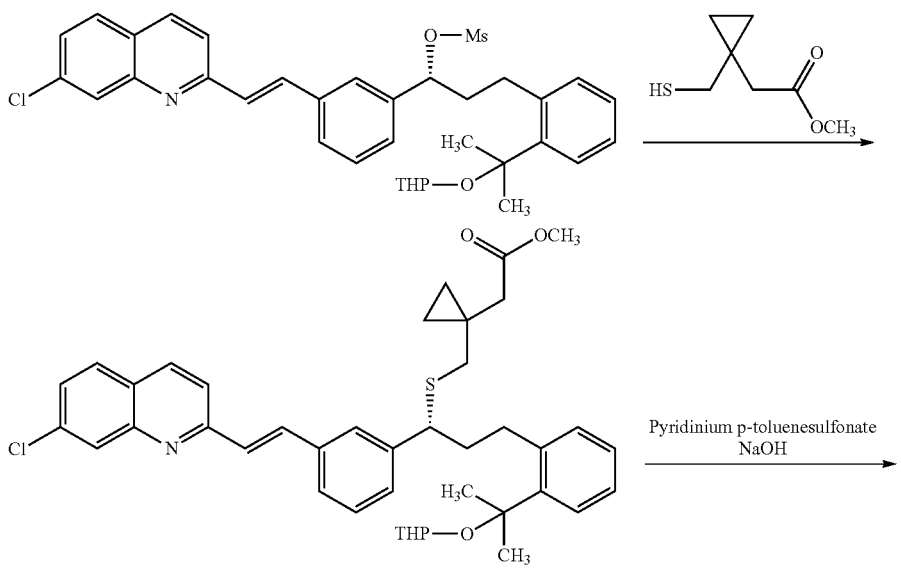

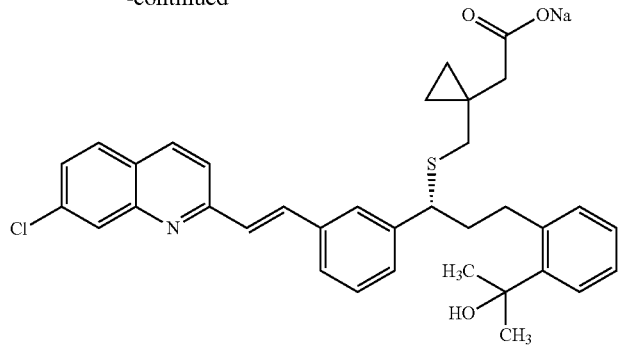

U.S. Pat. No. 5,614,632 ("the '632 patent") discloses a process for the preparation of montelukast sodium and its process intermediates. The process involves reaction of 2-(2-(3(S)-(3-(2(7-chloro-2-quinolinyl)-ethenyl)phenyl)-3-hydroxypropyl)phenyl)-2-propanol (diol compound) with methane sulfonyl chloride in toluene and acetonitrile at temperature −35° C. and isolating the corresponding mesylate compound as crystalline compound by filtration and slurry wash with n-hexane followed by drying under nitrogen atmosphere. The crystalline mesylate compound obtained was condensation with 1-(mercaptomethyl)cyclopropaneacetic acid in presence of butyl lithium to yield montelukast acid, which is isolated as montelukast amine salt such as dicyclohexylamine salt and followed by the amine salt is converted in to crystalline montelukast sodium. It is mentioned by the inventors of the '632 patent that the crystalline montelukast dicyclohexylamine salt offers an efficient method for the purification of montelukast, which circumvents the need to use chromatographic purification. However, the '632 patent use multiple solvents for example use of toluene, acetonitrile and hexane during the preparation and isolation of mesylate compound, resulting an increase in the manufacturing cost.

Further, the crystalline mesylate compound used in the '632 patent is very unstable under normal atmospheric conditions and throughout the reaction to produce the mesylate compound must be performed at a low temperature of about −30° C. and the product is required to store at extremely sensitive conditions such as store at about −20° C. under nitrogen atmosphere; thus the process is not viable for large scale production of montelukast sodium.

The process disclosed in the '632 patent is schematically represented as follows:

Scheme 2

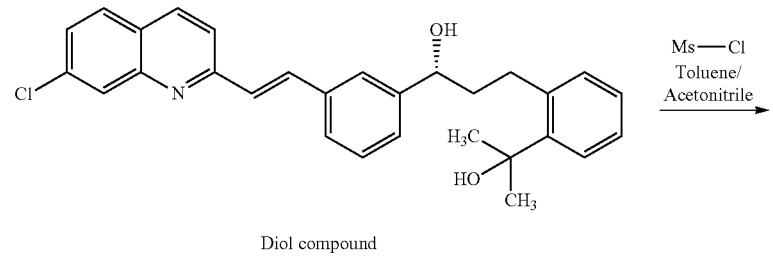

Diol compound

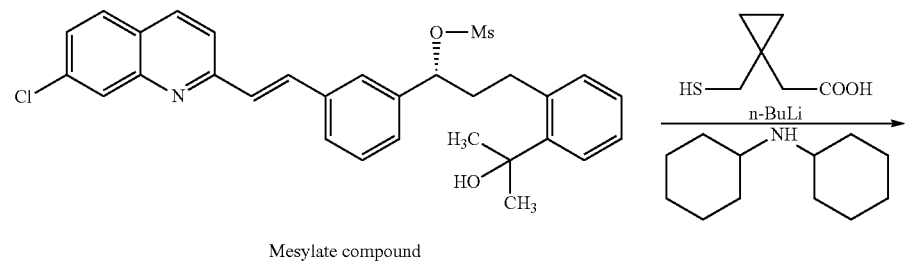

Mesylate compound

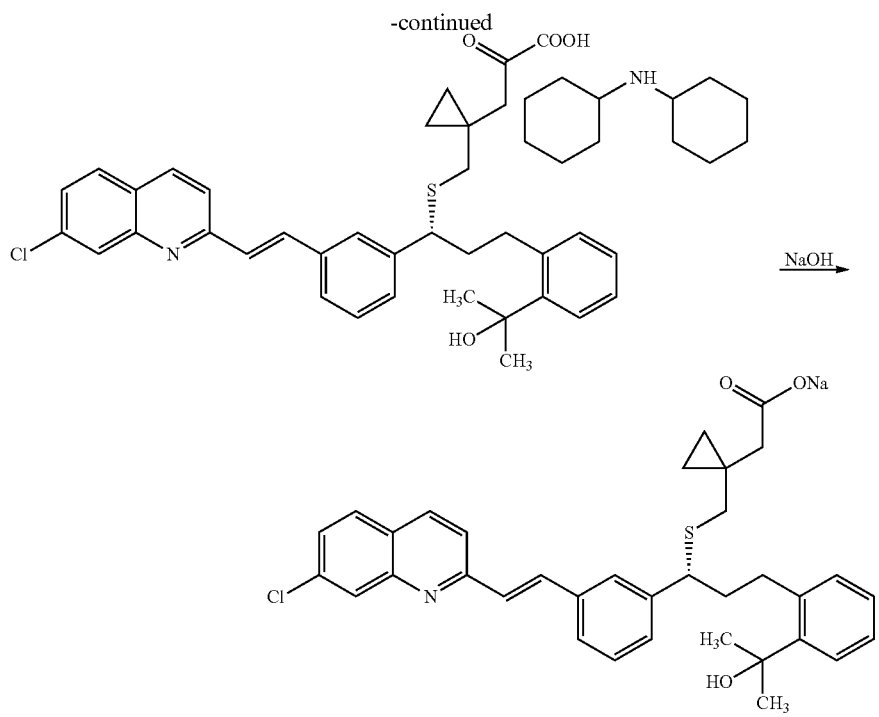

U.S. Pat. No. 7,547,787 ("the '787 patent") discloses a process for the preparation of montelukast sodium by reaction of montelukast diol compound with methane sulfonyl chloride in presence of diisopropylamine in tetrahydrofuran to obtain mesylate compound, which is in solution further directly reacted with 1-(mercaptomethyl)cyclopropane acetic acid methyl ester in a co-solvent such as dimethyl formamide, acetonitrile, N-methyl pyrrolilidone or dimethyl acetamide in presence of a base such as 47% sodium hydroxide solution, followed by hydrolysis of the resulting product to obtain montelukast sodium.

The '787 patent involves use of alkyl esters of 1-(mercaptomethyl)cyclopropane acetic acid, which adds an extra synthetic steps to the total synthesis of montelukast sodium such as esterification of the corresponding acid compound and hydrolysis of the esters, resulting in a process that is expensive in large scale production of montelukast sodium.

Moreover, the '787 patent teaches that the purity and yield of the montelukast sodium produced by the above method are 91% and 50% respectively. Extensive purification procedures are required in order to obtain the necessary quality of the end product and results low product thereby making the process quite expensive.

PCT Publication No. 2009/048236 ("the '236 publication") discloses a process for the preparation of montelukast sodium by reaction of mesylate compound with bis-alkali metal salt 1-(mercaptomethyl)cyclopropane acetic acid in a solvent mixture of ionic liquid and dimethyl sulfoxide (DMSO) to obtain montelukast free acid as solid compound, which is further converted to its sodium salt. The '236 publication process has certain disadvantages such as use of ionic liquids and involves additional process step of isolation of montelukast free acid in solid form, which in turn result to an increase in the manufacturing cost.

PCT Publication No. 2009/138993 ("the '993 publication") discloses a process to prepare montelukast sodium through use of phosphoric acid ester in place of unstable methane sulfonyl group of diol compound, which is reacted with alkyl ester of 1-(mercaptomethyl)cyclopropane acetic acid.

U.S. Pat. No. 8,178,680 ("the '680 patent") discloses a process to prepare montelukast sodium by reaction of mesylate compound with 1-(mercaptomethyl)cyclopropane acetic acid in dimethyl sulfoxide in presence of a base such as sodium methoxide solution in methanol, followed by hydrolysis of the resulting product with water, basification with sodium hydroxide and then repeated solvent washings and extractions using toluene and ethyl acetate finally isolating the montelukast as an amine salt, and further conversion it into montelukast sodium.

The '680 patent involves tedious workup procedures such as solvent washings and extractions to isolate the required product and thus results in excess time cycle, which in turn rendering the process quite expensive.

Processes for the preparation of montelukast and/or its salts by using solid montelukast free acid are disclosed in various literatures for example WO 2004/108679, US2005/107612, WO 2005/74935, US 2005/107426, WO 2009/117381. Isolation of solid montelukast free acid in the preparation of montelukast sodium involves additional process steps such as filtration, drying and storage etc requires more labor and more operational occupancy, which in turn result to an increase in the manufacturing cost, particularly on large scale production of montelukast sodium.

The processes for the production of montelukast and/or its salts by using different amine salts were discussed for example in US 2005/107612, US 2006/004204, WO 2004/108679, WO 2006/008751, WO 2006/043846, WO 2007/004237, WO 207/069261, WO 2007/072114, WO 2007/088545, WO 2007/96875, WO 2007/96889, WO 2007/107297, WO 2007/116240, WO 2008/001213, WO 2008/009970, WO 2008/015703, WO 2008/017669, WO 2008/023044, WO 2008/032099, WO 2008/058118, WO 2008/062478, WO 2008/87628, WO 2008/126075, WO 2008/

136693, WO 2009/06861, WO 2009/027990, WO 2009/052625, WO 2009/113087, WO 2009/117381, WO 2009/053424, WO 2009/098271, WO 2010/036048, WO 2010/064257, WO 2011/004298, WO 2011/076237, WO 2012/015255.

Our U.S. Pat. No. 8,207,343 discloses process for the preparation of montelukast sodium through use of 1-methyl-3-phenylpropyl amine salt of montelukast.

Although many processes have been described in the art for the preparation of montelukast and its salt thereof, there still remains a need for a process for manufacturing montelukast and their salts, which has minimal steps that avoids additional synthetic steps as described above on one hand and avoiding the use of chromatographic purification and hazardous reagents, improves the yield and quality of montelukast sodium.

OBJECT OF THE INVENTION

The main object of the invention is to provide a simple, cost effective process for the preparation of montelukast sodium with high purity and yield without the formation of undesired impurities.

Another object of the invention is to provide a process for the preparation of montelukast sodium wherein the process excludes the use of multiple solvents.

Yet object of the invention is to reduce the steps of the reaction by eliminating the step of isolating the less stable solid mesylate compound and further eliminating solid montelukast free acid, thereby reducing the overall reaction time cycle, making the process more suitable for commercial applications.

SUMMARY OF THE INVENTION

The present invention encompasses an improved process for the preparation of montelukast and salts thereof with high product yield and quality.

In one embodiment, the present invention provides an improved process for the preparation of montelukast sodium, comprising the steps of:
a) reacting 2-(2-(3(S)-(3-(2-(7-chloro-2-quinolinyl)-ethenyl)phenyl)-3-hydroxypropyl)phenyl)-2-propanol(diol compound) with methane sulfonyl chloride in an organic solvent in presence of a base to obtain a solution of 2-(2-(3(S)-(3-(2-(7-chloro-2-quinolinyl)-ethenyl)phenyl)-3-methanesulfonyloxy propyl)phenyl)-2-propanol(mesylate compound),
b) reacting 1-(mercaptomethyl)cyclopropane acetic acid with a base and optionally an additional alkali source in a polar aprotic solvent to obtain a solution of dibase salt of 1-(mercaptomethyl)cyclopropane acetic acid,
c) reacting the solution of 2-(2-(3(S)-(3-(2-(7-chloro-2-quinolinyl)-ethenyl)phenyl)-3-methanesulfonyloxy-propyl)phenyl)-2-propanol(mesylate compound) of step a) with the solution of dibase salt of 1-(mercaptomethyl)cyclopropane acetic acid of step b),
d) isolating the montelukast obtained from step c) with an organic amine to obtain montelukast amine salt,
e) optionally purifying the montelukast amine salt with an organic solvent,
f) converting the montelukast amine salt in to montelukast sodium.

In another embodiment, the present invention provides an improved process for the preparation of montelukast sodium, comprising the steps of:
a) reacting 2-(2-(3(S)-(3-(2-(7-chloro-2-quinolinyl)-ethenyl) phenyl)-3-hydroxypropyl)phenyl)-2-propanol (diol compound) with methane sulfonyl chloride in an organic solvent in presence of a base to obtain a solution of 2-(2-(3(S)-(3-(2-(7-chloro-2-quinolinyl)-ethenyl)phenyl)-3-methanesulfonyloxy propyl)phenyl)-2-propanol (mesylate compound),
b) reacting 1-(mercaptomethyl)cyclopropane acetic acid with a base and an additional alkali source in a polar aprotic solvent to obtain a solution of dibase salt of 1-(mercaptomethyl)cyclopropane acetic acid,
c) reacting the solution of 2-(2-(3(S)-(3-(2-(7-chloro-2-quinolinyl)-ethenyl)phenyl)-3-methanesulfonyloxy-propyl)phenyl)-2-propanol(mesylate compound) of step a) with the solution of dibase salt of 1-(mercaptomethyl)cyclopropane acetic acid of step b),
d) isolating the montelukast obtained from step c) with an organic amine to obtain montelukast amine salt,
e) optionally purifying the montelukast amine salt with an organic solvent,
f) converting the montelukast amine salt in to montelukast sodium.

In another embodiment, the present invention provides an improved process for the preparation of montelukast sodium, comprising the steps of:
a) reacting 2-(2-(3(S)-(3-(2-(7-chloro-2-quinolinyl)-ethenyl) phenyl)-3-hydroxypropyl)phenyl)-2-propanol(diol compound) with methane sulfonyl chloride in an organic solvent in presence of a base to obtain a solution of 2-(2-(3(S)-(3-(2-(7-chloro-2-quinolinyl)-ethenyl)phenyl)-3-methanesulfonyloxy propyl)phenyl)-2-propanol(mesylate compound),
b) reacting 1-(mercaptomethyl)cyclopropane acetic acid with a base and an additional alkali source in a polar aprotic solvent to obtain a solution of dibase salt of 1-(mercaptomethyl)cyclopropane acetic acid,
c) reacting the solution of 2-(2-(3(S)-(3-(2-(7-chloro-2-quinolinyl)-ethenyl) phenyl)-3-methanesulfonyloxy-propyl)phenyl)-2-propanol(mesylate compound) of step a) with the solution of dibase salt of 1-(mercaptomethyl)cyclopropane acetic acid of step b),
d) isolating the montelukast obtained from step c) with 1-methyl-3-phenylpropyl amine to obtain montelukast 1-methyl-3-phenylpropyl amine salt,
e) optionally purifying the montelukast 1-methyl-3-phenylpropyl amine salt with an organic solvent,
f) converting the montelukast 1-methyl-3-phenylpropyl amine salt in to montelukast sodium.

In another embodiment, the organic solvent in step a) is selected from the group consisting of dimethylformamide, dimethyl sulphoxide, dimethyl acetamide, dichloro methane, toluene, xylenes, tetrahydrofuran, 2-methyl tetrahydrofuran, acetonitrile and mixtures thereof; preferably the organic solvent is tetrahydrofuran.

The base used for step a) reaction is typically an organic amine. The organic amine includes but are not limited to triethylamine, triisobutylamine, N,N-diisopropylethylamine (DIPEA), N,N-dimethylaniline, N-methylmorpholine, N-methylpyrrolidine, Pyridine; or combinations thereof; preferably the base comprises N,N-diisopropylethylamine.

In another embodiment, the polar aprotic solvent in step b) is selected from dimethyl formamide, dimethyl acetamide, acetone, methanol, acetonitrile, dimethyl sulfoxide, tetrahydrofuran, dichloromethane, ethyl acetate and mixtures thereof; preferably the polar aprotic solvent is tetrahydrofuran, dimethyl formamide or mixtures thereof.

In another embodiment, the base in step b) is a strong base. Preferably the base is selected from the group consisting of sodium hydride, lithium hydride, sodium hydroxide, sodium methoxide, lithium methoxide, butyl lithium, potassium tertiary butoxide or quarternary ammonium bases; preferably the base is sodium methoxide.

In another embodiment, the additional alkali source used is selected from sodium hydroxide, potassium hydroxide, sodium tertiary butoxide, potassium tertiary butoxide and the like and mixtures thereof; preferably aqueous sodium hydroxide.

In a preferred embodiment, the step c) reaction is carried out by adding step a) solution into step b) solution.

In a preferred embodiment, the step c) reaction is carried out by adding step b) solution into step a) solution.

In a preferred embodiment, step a) to step c) are carried out in a one step reaction, prior to saltification step; where the intermediate steps are not isolated as solid.

In another embodiment, the present invention is best described with the following reaction scheme:

DETAILED DESCRIPTION OF THE INVENTION

The present invention provides an improved process for the preparation of montelukast sodium with high product yield and quality. In particular, the present invention provides a process to prepare montelukast sodium, wherein the process includes without isolation of the less stable intermediates such as solid mesylate compound and avoiding cumbersome chromatographic techniques.

In one embodiment, the present invention provides an improved process for the preparation of montelukast sodium, comprising the steps of:

a) reacting 2-(2-(3(S)-(3-(2-(7-chloro-2-quinolinyl)-ethenyl)phenyl)-3-hydroxypropyl)phenyl)-2-propanol(diol compound) with methane sulfonyl chloride in an organic solvent in presence of a base to obtain a solution of 2-(2-(3(S)-(3-(2-(7-chloro-2-quinolinyl)-ethenyl)phenyl)-3-methanesulfonyloxy propyl)phenyl)-2-propanol(mesylate compound),

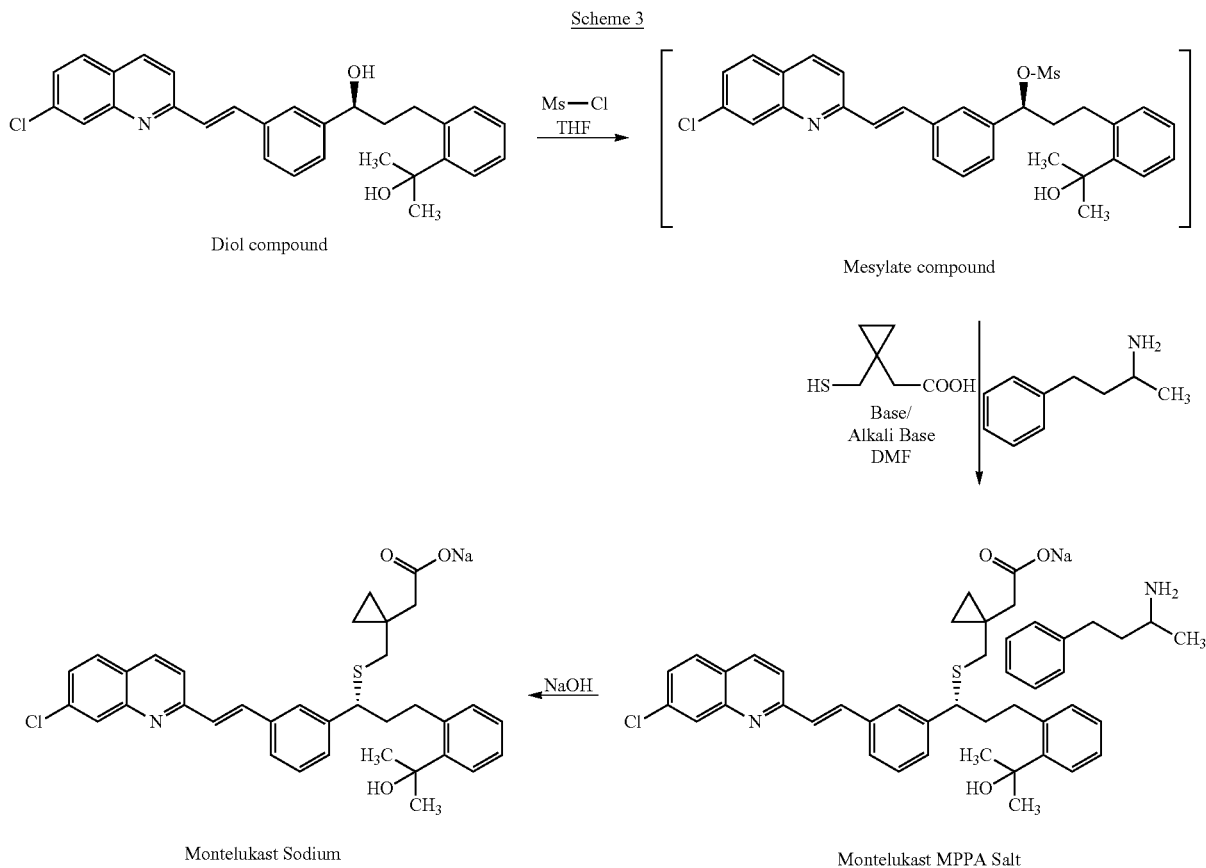

Scheme 3 b) reacting 1-(mercaptomethyl)cyclopropane acetic acid with a base and optionally an additional alkali source in a polar aprotic solvent to obtain a solution of dibase salt of 1-(mercaptomethyl)cyclopropane acetic acid, c) reacting the solution of 2-(2-(3(S)-(3-(2-(7-chloro-2-quinolinyl)-ethenyl) phenyl)-3-methanesulfonyloxy-propyl)phenyl)-2-propanol(mesylate compound) of step a) with the solution of dibase salt of 1-(mercaptomethyl)cyclopropane acetic acid of step b),

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 is the characteristic powder X-ray diffraction (XRD) pattern of montelukast 1-methyl-3-phenylpropyl amine salt.

d) isolating the montelukast obtained from step c) with an organic amine to obtain montelukast amine salt, e) optionally purifying the montelukast amine salt with an organic solvent, f) converting the montelukast amine salt in to montelukast sodium.

In another embodiment, the present invention provides an improved process for the preparation of montelukast sodium, comprising the steps of:

a) reacting 2-(2-(3(S)-(3-(2-(7-chloro-2-quinolinyl)-ethenyl)phenyl)-3-hydroxypropyl)phenyl)-2-propanol(diol compound) with methane sulfonyl chloride in an organic solvent in presence of a base to obtain a solution of 2-(2-(3(S)-(3-(2-(7-chloro-2-quinolinyl)-ethenyl)phenyl)-3-methanesulfonyloxy propyl)phenyl)-2-propanol(mesylate compound), b) reacting 1-(mercaptomethyl)cyclopropane acetic acid with a base and an additional alkali source in a polar aprotic solvent to obtain a solution of dibase salt of 1-(mercaptomethyl)cyclopropane acetic acid, c) reacting the solution of 2-(2-(3(S)-(3-(2-(7-chloro-2-quinolinyl)-ethenyl)phenyl)-3-methanesulfonyloxy-propyl)phenyl)-2-propanol(mesylate compound) of step a) with the solution of dibase salt of 1-(mercaptomethyl)cyclopropane acetic acid of step b), d) isolating the montelukast obtained from step c) with an organic amine to obtain montelukast amine salt, e) optionally purifying the montelukast amine salt with an organic solvent, f) converting the montelukast amine salt in to montelukast sodium.

The starting material 2-(2-(3(S)-(3-(2-(7-chloro-2-quinolinyl)-ethenyl)phenyl)-3-hydroxypropyl)phenyl)-2-propanol(diol compound) is known in the art and can be prepared by any known method, for example starting diol compound may be synthesized as disclosed in U.S. Pat. No. 5,565,473.

Step a) of reacting diol compound with methanesulfonyl chloride preferably includes: admixing the diol compound with an organic solvent; optionally cooling to reduced temperature of about −30° C. to about 10° C. and adding a base; adding methanesulfonyl chloride and reacting for sufficient time period to allow completing the reaction; filtering the thus formed suspension and obtaining a filtrate containing the mesylate product; and using the filtrate in the next reaction without isolating it in to the solid compound.

The organic solvent used in the reaction can be selected from dimethylformamide, dimethylsulphoxide, dimethyl acetamide, dichloromethane, toluene, xylenes, tetrahydrofuran, 2-methyl tetrahydrofuran, acetonitrile and mixtures thereof; preferably the organic solvent comprises tetrahydrofuran.

The base used for step a) reaction is typically an organic amine. The organic amine includes but are not limited to triethylamine, triisobutylamine, N,N-diisopropylethylamine (DIPEA), N,N-dimethylaniline, N-methylmorpholine, N-methylpyrrolidine, pyridine; or combinations thereof; preferably the base comprises N,N-diisopropylethylamine.

The methanesulfonyl chloride can be added to the cooled mixture of base and diol compound. The addition can be drop-wise or at least two equal portions. The methanesulfonyl chloride can be added in three portions, four portions or five portions; preferably methane sulfonyl chloride can be added in a drop wise manner.

In a specific embodiment, the mesylate compound obtained from step a) is as such solution is used further reaction with dibase salt of 1-(mercaptomethyl)cyclopropane acetic acid, without isolating into solid compound, thereby avoiding further operational steps such as filtration, drying and storage of less stable mesylate compound.

Step b) of reacting 1-(mercaptomethyl)cyclopropane acetic acid with a base and optionally an additional alkali source preferably includes: mixing the 1-(mercaptomethyl) cyclopropane acetic acid with a polar aprotic solvent; optionally cooling to reduced temperature of about 0° C. to about −15° C. and adding base and optionally an additional alkali source, preferably a premixed solution of base and an additional alkali source and reacting for sufficient time period to allow completing the reaction.

The polar aprotic solvent used in the reaction can be selected from dimethyl formamide, dimethyl acetamide, methanol, acetone, acetonitrile, dimethyl sulfoxide, tetrahydrofuran, dichloromethane, ethyl acetate and mixtures thereof; preferably the organic solvent is tetrahydrofuran, dimethyl formamide or mixtures thereof.

The base used for step b) is a strong base. Preferably the base is selected from the group consisting of sodium hydride, lithium hydride, sodium hydroxide, sodium methoxide, lithium methoxide, butyl lithium, potassium tertiary butoxide or quarternary ammonium bases; preferably the base is sodium methoxide.

The additional alkali source used is selected from sodium hydroxide, potassium hydroxide, sodium tertiary butoxide, potassium tertiary butoxide and the like and mixtures thereof; preferably aqueous sodium hydroxide.

Step c) of reacting mesylate compound with the dibase salt of 1-(mercaptomethyl)cyclopropane acetic acid, preferably disodium salt of 1-(mercaptomethyl)cyclopropane acetic acid preferably includes: by adding step a) reaction solution comprising mesylate compound and tetrahydrofuran in to step b) reaction solution comprising dimethyl formamide solution of disodium salt of 1-(mercaptomethyl) cyclopropane acetic acid; stirring for sufficient time period to allow completing the reaction; and isolating the resultant montelukast acid as organic amine salt.

The step c) reaction is carried out at a temperature of about −20° C. to about 10° C.; preferably at about −5° C. to about 0° C.

In a specific embodiment, the present invention provides a process for the preparation of montelukast from diol compound to montelukast amine salt of step c), where the steps a) to c) are carried out without isolating intermediates as solid, prior to saltification step c).

After completion of the reaction, montelukast product can be isolated from the reaction mass by quenching the reaction mixture in to saturated sodium chloride solution and water immiscible organic solvent and then treated with an acid followed by obtained montelukast acid is converted in to an amine salt.

The acid can be either an inorganic acid or an organic acid. Specific organic acids include, but are not limited to, acetic acid, propionic acid, oxalic acid, benzoic acid, maleic acid, malonic acid, fumaric acid, tartaric acid, malic acid, citric acid, and combinations thereof; preferably the acid comprises tartaric acid.

The water immiscible organic solvent can be selected from the group consisting of methyl acetate, ethyl acetate, n-propyl acetate, isopropyl acetate, n-butyl acetate, isobutyl acetate, chloroform, dichloromethane, toluene xylene or mixtures thereof. Preferably, the organic solvent comprises toluene or ethyl acetate.

The montelukast, amine salt preferably dicyclohexyl amine, 1-methyl-3-phenylpropyl amine and the like; more preferably montelukast 1-methyl-3-phenylpropyl amine salt can be prepared by mixing 1-methyl-3-phenylpropyl amine and the montelukast as obtained above at a temperature of about 25° C. to about 95° C. in a suitable organic solvent, optionally adding seed material of montelukast 1-methyl-3-phenylpropyl amine salt and isolating the montelukast 1-methyl-3-phenylpropyl amine salt. The montelukast 1-methyl-3-phenylpropyl amine salt obtained is optionally purified before proceed to montelukast sodium.

Suitable organic solvent include, but is not limited to $C_{1-4}$ alcohols such as methanol, ethanol, isopropanol, n-propanol and the like; ketones such as acetone, methyl ethyl ketone, methyl isobutyl ketone and the like; esters such as ethyl acetate, isopropyl acetate and the like; ethers such as isopropyl ether, methyl ethyl ether, tetrahydrofuran, 1,4-dioxane and the like; aromatic hydrocarbons such as toluene, xylene and the like; cyclic hydrocarbons such as n-hexane, n-heptane, cyclohexane and the like; water and mixtures thereof; preferably the suitable organic solvent is selected from ethyl acetate, toluene, n-hexane, n-heptane or cyclohexane.

The montelukast 1-methyl-3-phenylpropyl amine salt can be purified by mixing montelukast 1-methyl-3-phenylpropyl amine salt with a suitable organic solvent preferably includes:
 i) dissolving montelukast 1-methyl-3-phenylpropyl amine salt in a suitable organic solvent as defined just above at a temperature of about 25° C. to about reflux;
 ii) stirring for about 30 minutes,
 iii) cooling to precipitation to about 25° C.,
 iv) filtering the montelukast 1-methyl-3-phenylpropyl amine salt; wherein the suitable organic solvent is defined as above, preferably toluene.

Step f) of converting the montelukast amine salt preferably 1-methyl-3-phenylpropyl amine salt in to montelukast sodium by generating the montelukast free acid from montelukast amine salt by neutralizing the amine in the presence of an organic acid, preferably acetic acid in halogenated solvents, for example, chloroform, dichloromethane or dichloroethane, preferably, dichloromethane, or an aromatic hydrocarbon, for example toluene.

Then, converting the obtained montelukast acid in solution in to sodium salt of montelukast by adding sodium source such as sodium hydroxide, sodium methoxide or sodium ethoxide in alcohols such as methanol, ethanol, propanol, butanol, 2-propanol or tertiary butanol and mixtures thereof; preferably ethanolic sodium hydroxide. The montelukast sodium thus obtained can be isolated by conventional techniques such as by crystallization, solvent precipitation, concentrated by subjecting the solution to heating, spray drying, evaporation on rotary evaporator under vacuum, agitated thin film dryer (ATFD) and the like. Preferably, the reaction solvent may be concentrated and adding hydrocarbon solvent such as n-heptane to the obtained residue such that the montelukast sodium can be recovered by conventional techniques, for example filtration.

The present invention provides a montelukast sodium, obtained by the process described herein, having a chiral purity of at least about 98% as measured by chiral HPLC, preferably at least about 99% as measured by chiral HPLC; more preferably at least about 99.9% as measured by chiral HPLC; cyclic ether impurity of Formula A is less than 0.1% as measured by HPLC; sulfoxide impurity of Formula B is less than about 0.15% as measured by HPLC; styrene impurity of Formula C is less than about 0.15% as measured by HPLC; montelukast cis isomer is less than about 0.05%; diol compound of less than about 0.1% as measured by HPLC; Michael impurities of Formula D & Formula E are less than about 0.1% as measured by HPLC.

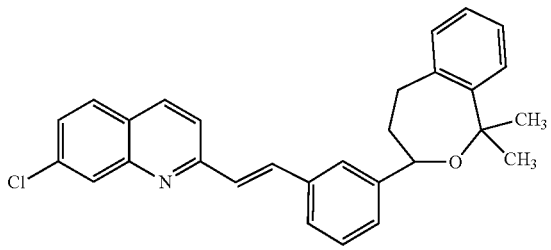

Formula A

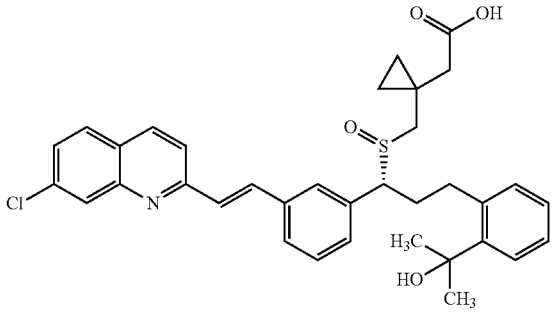

Formula B

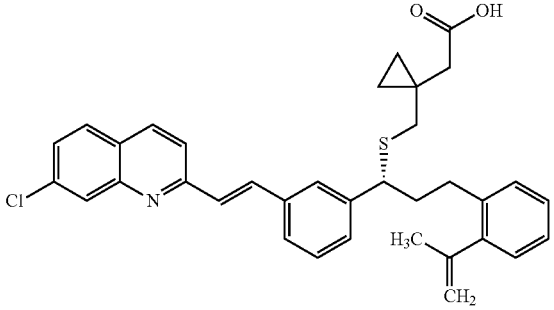

Formula C

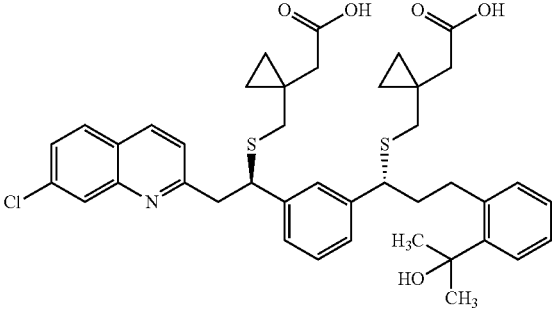

Formula D

-continued

Formula E

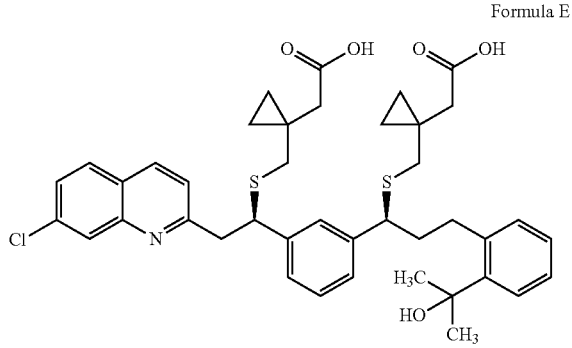

The montelukast sodium obtained by the process of the present invention is amorphous form and free flowing and non-solvated solid; hence it is well suited for pharmaceutical applications.

EXAMPLES

The following non limiting examples illustrate specific embodiments of the present invention. They are not intended to be limiting the scope of the present invention in any way.

Example 1

Preparation of Montelukast 1-methyl-3-phenylpropyl Amine Salt

A 1 L round bottom flask fitted with a mechanical stirrer, thermometer socket, addition funnel was purged with $N_2$. The flask was charged 2-(2-(3(S)-(3-(2-(7-chloro-2-quinolinyl)-ethenyl)phenyl)-3-hydroxypropyl)phenyl)-2-propanol (100 gms) and THF (500 ml) and temperature was cooled to about −20° C. to about −15° C. Diisopropyl ethyl amine (42.4 gms) was charged and then methane sulfonyl chloride (30 gms) was added. The reaction mixture was stirred for 4 hours and undissolved salts were filtered off from the reaction to obtain filtrate containing mesylate compound. In another 2 L round bottom flask was charged 1-(mercaptomethyl)cyclopropane acetic acid (41.5 gms) and THF (400 ml) at 25° C. to 35° C. and the temperature was cooled to about −15° C. 15% w/w butyl lithium (355 ml) solution in hexane was added at about −15° C. to about −10° C. and the reaction mixture was stirred for 2 hours at same temperature to obtain the solution of dilithium salt of 1-(mercaptomethyl)cyclopropane acetic acid. The solution of mesylate compound was charged in to the solution of dilithium salt of 1-(mercaptomethyl)cyclopropane acetic acid at about −15° C. to about −5° C. and the reaction mixture was stirred for about 10 hours at about −5° C. After completion of the reaction, the reaction mixture was quenched in to mixture of 5% NaCl solution and toluene (1000 ml) and the layers were separated and the aqueous layer was extracted with toluene (500 ml). The total organic layer was washed with 5% L (+)-tartaric acid (500 ml) and the organic layer was separated. The organic layer was washed with water (1000 ml) and the solvent was evaporated until about 800 ml remains in the flask under vacuum at below 50° C. The solution was cooled to about 30° C. and was charged 1-methyl-3-phenylpropyl amine (39.1 gms) at 25° C. to 35° C. Stirred for about 24 hours and precipitated solid was filtered and washed with toluene (100 ml). The wet product was dried at about 50° C. to about 55° C. to provide the title compound as crude.

Yield: 115 gms.
HPLC purity: 97%
S-isomer content: Not detected
Cyclic ether: 0.3%
Diol: 0.7%

Example 2

Purification of Montelukast 1-methyl-3-phenylpropyl Amine Salt

A 2 L round bottom flask fitted with a mechanical stirrer, thermometer socket, addition funnel was purged with $N_2$. The flask was charged 100 gms of Montelukast 1-methyl-3-phenylpropyl amine salt (obtained from Example 1) and toluene (1000 ml). The temperature was raised to 70° C. to 75° C. and stirred for 15 minutes. The reaction mixture was allowed to cool to 25° C. to 35° C. and stirred for about 8 hours at same temperature. Precipitated solid was filtered and washed with toluene (10 ml). The wet product was dried at about 50° C. to about 55° C. under reduced pressure to provide the title compound as pure.

Yield: 90 gms
Cyclic ether impurity: 0.02%
Sulfoxide impurity: 0.10%
Styrene impurity: 0.12%
Cis isomer: 0.02%
S-isomer content: Not detected
Diol compound: 0.05%

Example 3

Preparation of Montelukast 1-Methyl-3-Phenylpropyl Amine Salt

A 1 L round bottom flask fitted with a mechanical stirrer, thermometer socket, addition funnel was purged with $N_2$. The flask was charged 2-(2-(3(S)-(3-(2-(7-chloro-2-quinolinyl)-ethenyl)phenyl)-3-hydroxypropyl)phenyl)-2-propanol (100 gms) and THF (500 ml) and temperature was allowed to cool to about −20° C. to about −15° C. Diisopropyl ethyl amine (45.2 gms) was charged and then methane sulfonyl chloride (32.5 gms) was added at same temperature. The reaction mixture was stirred for 4 hours and undissolved salts were filtered off to obtain filtrate containing mesylate compound. In another 2 L round bottom flask was charged 1-(mercaptomethyl)cyclopropane acetic acid (38.35 gms) and DMF (300 ml) at 25° C. to 35° C. and allowed to cool to about −5° C. to 0° C. To the reaction mixture, a mixture of 25% w/w Sodium methoxide (130 ml) solution in methanol and C.S. Lye (13 ml) was added at same temperature and the reaction mixture was stirred for 2 hours at same temperature to obtain the solution of disodium salt of 1-(mercaptomethyl)cyclopropane acetic acid. The solution of mesylate compound was charged in to the solution of disodium salt of 1-(mercaptomethyl)cyclopropane acetic acid at about −5° C. to about 0° C. and the reaction mixture was stirred for about 12 hours at about 0° C. to about 5° C. After completion of the reaction, the reaction mixture was quenched in to mixture of 5% NaCl solution and ethyl acetate (800 ml). The organic layer was washed with 5% L (+)-tartaric acid (500 ml) followed by 5% Sodium chloride solution. The organic layer was evaporated to about 50% of the volume under vacuum at below 50° C. then allowed to cool to about 25° C. to 35° C. 1-methyl-3-phenylpropyl amine (39.1 gms) was added at 25° C. to 35° C. and stirred for about 12 hours at same temperature followed by n-hexane (1200 ml) was added and stirred for 6 hrs at about 25° C. to 35° C. The precipitated solid was filtered and dried at 50-55° C. for 12 hrs to provide the title compound as crude.
Yield: 130 gms.
HPLC purity: 97.47%
S-isomer content: Not detected
Cyclic ether: 0.2%
Styrene impurity: 0.25%
Diol: 0.23%
Formula D: 0.52%
Formula E: 0.57%

Example 4

Preparation of Montelukast 1-methyl-3-phenylpropyl Amine Salt

A 1 L round bottom flask fitted with a mechanical stirrer, thermometer socket, addition funnel was purged with $N_2$. The flask was charged 2-(2-(3(S)-(3-(2-(7-chloro-2-quinolinyl)-ethenyl)phenyl)-3-hydroxypropyl)phenyl)-2-propanol (100 gms) and THF (500 ml) and temperature was allowed to cool to about −20° C. to about −15° C. Diisopropyl ethyl amine (45.2 gms) was charged and then methane sulfonyl chloride (32.5 gms) was added at same temperature. The reaction mixture was stirred for 4 hours and undissolved salts were filtered off to obtain filtrate containing mesylate compound. In another 2 L round bottom flask was charged 1-(mercaptomethyl)cyclopropane acetic acid (38.35 gms) and DMF (300 ml) at 25° C. to 35° C. and allowed to cool to about −5° C. to 0° C. To the reaction mixture, a mixture of 25% w/w Sodium methoxide (130 ml) solution in methanol and C.S. Lye (13 ml) was added at same temperature and the reaction mixture was stirred for 2 hours at same temperature to obtain the solution of disodium salt of 1-(mercaptomethyl)cyclopropane acetic acid. The obtained solution was charged in to the solution of mesylate compound at about −5° C. to about 0° C. and the reaction mixture was stirred for about 12 hours at about 0° C. to about 5° C. After completion of the reaction, the reaction mixture was quenched in to mixture of 5% NaCl solution and ethyl acetate (800 ml). The organic layer was washed with 5% L (+)-tartaric acid (500 ml) followed by 5% Sodium chloride solution. The organic layer was evaporated to about 50% of the volume under vacuum at below 50° C. then allowed to cool to about 25° C. to 35° C. 1-methyl-3-phenylpropyl amine (39.1 gms) was charged at 25° C. to 35° C. and stirred for about 12 hours at same temperature followed by n-hexane (1200 ml) was added and stirred for 6 hrs at about 25° C. to 35° C. The precipitated solid was filtered and dried at 50-55° C. for 12 hrs to provide the title compound as crude.
Yield: 125 gms.
HPLC purity: 96.2%
S-isomer content: Not detected
Cyclic ether: 0.31%
Styrene impurity: 0.27%
Diol: 0.4%
Formula D: 0.62%
Formula E: 0.55%

Example 5

Purification of Montelukast 1-methyl-3-phenylpropyl Amine Salt

A 2 L round bottom flask fitted with a mechanical stirrer, thermometer socket, addition funnel was purged with $N_2$. The flask was charged 1200 ml of toluene and heated to 70 to 75° C. At this temperature charged 120 gms of Montelukast 1-methyl-3-phenylpropyl amine salt (Obtained from Example 3) and stirred for 5 mins. The reaction mixture was allowed to cool to 25° C. to 35° C. and stirred for about 8 hours at same temperature. Precipitated solid was filtered and washed with toluene (120 ml) to obtain wet product. The wet product was dried at about 50° C. to about 55° C. under reduced pressure to provide the title compound as pure.
Yield: 106 gms
Cyclic ether impurity: 0.06%
Sulfoxide impurity: 0.04%
Styrene impurity: 0.15%
Cis isomer: 0.01%
S-isomer content: Not detected
Diol compound: Not detected
Formula D: 0.05%
Formula E: 0.07%

Example 6

Preparation of Montelukast Sodium

A 3 L round bottom flask fitted with a mechanical stirrer, thermometer socket, addition funnel was purged with $N_2$. The flask was charged 100 gms of montelukast 1-methyl-3-phenylpropyl amine salt (obtained from Example 5) and dichloromethane (800 ml) and water (500 ml) at about 25° C. to about 30° C. Reaction mass pH was adjusted to about 4.0 to 4.5 with 1:1 aqueous acetic acid (about 40 ml). Organic layer was separated and aqueous layer was extracted with dichloromethane (300 ml). The combined organic layer was washed with water (2×600 ml) and to the organic layer ethanolic sodium hydroxide solution (5.33 gms of sodium hydroxide pellets dissolved in 274 ml of ethanol and 2.7 ml of water) was added and stirred for 30 minutes. Dichloromethane was distilled completely at below 40° C. to get a residue. Then methanol (800 ml) was charged, stirred at 40° C. to 45° C. for 30 minutes, treated with activated carbon and filtered. The filtrate was distilled out completely under reduced pressure below 45° C. n-heptane (200 ml) was charged to the above residue and distilled out methanol traces completely below 45° C. Again n-heptane (500 ml) was added and stirred for 4 hours at 25° C. to 35° C. Precipitated solid was filtered and washed with n-heptane (100 ml) and the wet product was dried at about 85° C. to about 95° C. under reduced pressure to provide the title compound.
Yield: 74 gms
Cyclic ether impurity: 0.02%
Sulfoxide impurity: 0.1%
Styrene impurity: 0.14%
Cis isomer: 0.02%
S-isomer content: Not detected
Diol compound: Not detected
Formula D: 0.04%
Formula E: 0.05%

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the specification appended hereto.

We claim:

1. A process for preparing montelukast sodium of Formula I,

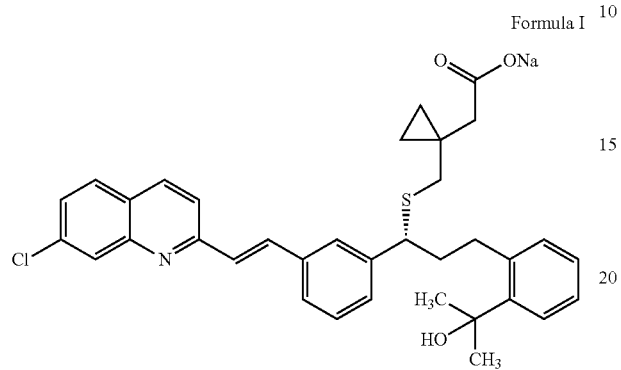

Formula I comprising the steps of:
a) reacting 2-(2-(3(S)-(3-(2-(7-chloro-2-quinolinyl)-ethenyl)phenyl)-3-hydroxy propyl)phenyl)-2-propanol (diol compound) of formula

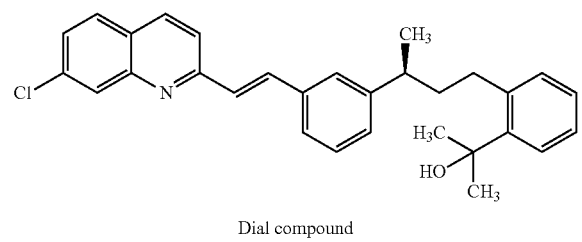 [SMILES: C[C@@H](CCc1ccccc1C(C)(C)O)c1cccc(/C=C/c2ccc3ccc(Cl)cc3n2)c1]

Dial compound with methane sulfonyl chloride in an organic solvent in the presence of a base to obtain a solution of 2-(2-(3(S)-(3-(2-(7-chloro-2-quinolinyl)-ethenyl) phenyl)-3-methanesulfonyloxypropyl)phenyl)-2-propanol (mesylate compound)

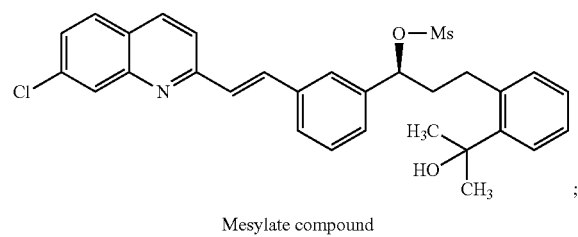 [SMILES: CC(C)(O)c1ccccc1CC[C@H](OS(C)(=O)=O)c1cccc(/C=C/c2ccc3ccc(Cl)cc3n2)c1]

Mesylate compound b) reacting 1-(mercaptomethyl)cyclopropane acetic acid

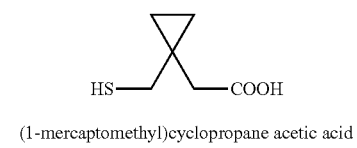

(1-mercaptomethyl)cyclopropane acetic acid with a base and an additional alkali source in a polar aprotic solvent to obtain a solution of dibase salt of 1-(mercaptomethyl)cyclopropane acetic acid;
c) reacting the mesylate compound of step a) with the dibase salt of 1-(mercaptomethyl)cyclopropane acetic acid of step b) at a temperature of about −20° C. to about 10° C. to obtain an montelukast intermediate;
d) converting the montelukast intermediate from step c) with an organic amine to obtain a montelukast amine salt; and
e) converting the montelukast amine salt from step d to montelukast sodium.

2. The process of claim 1, wherein the organic solvent of step a) is selected from the group consisting of dimethylformamide, dimethyl sulphoxide, dimethyl acetamide, dichloro methane, toluene, xylenes, tetrahydrofuran, 2-methyl tetrahydrofuran, acetonitrile, and combinations thereof.

3. The process of claim 1, wherein the base of step a) is selected from the group consisting of triethylamine, triisobutylamine, N,N-diisopropylethylamine, N,N-dimethylaniline, N-methylmorpholine, N-methylpyrrolidine, pyridine; and combinations thereof.

4. The process of claim 1, wherein the base of step b) is selected from the group consisting of sodium hydride, lithium hydride, sodium hydroxide, sodium methoxide, lithium methoxide, butyl lithium, potassium tertiary butoxide, quarternary ammonium bases, and combinations thereof.

5. The process of claim 1, wherein the alkali source of step b) is selected from the group consisting of sodium hydroxide, potassium hydroxide, sodium tertiary butoxide, potassium tertiary butoxide, and mixtures thereof.

6. The process of claim 1, wherein the polar aprotic solvent of step b) is selected from the group consisting of dimethyl formamide, dimethyl acetamide, acetone, methanol, acetonitrile, dimethyl sulfoxide, tetrahydrofuran, dichloromethane, ethyl acetate, and combinations thereof.

7. The process of claim 1, wherein the reaction of step c) is carried out by adding the solution of step a) to the solution of step b).

8. The process of claim 1, wherein products of steps a) to c) are not isolated.

9. The process of claim 1, wherein the reaction of step c) is carried out at a temperature of about −5° C. to about 0° C.

10. The process of claim 1, wherein the organic amine is 1-methyl-3-phenylpropyl amine, and the montelukast amine salt is montelukast 1-methyl-3-phenylpropyl amine salt.

11. The process of claim 1, further comprising the step of purifying the montelukast amine salt with an organic solvent after step d before step e.

12. The process of claim 10, further comprising the steps of:
i) dissolving montelukast 1-methyl-3-phenylpropyl amine salt in an organic solvent at a temperature of about 25° C. to about reflux;
ii) stirring for about 30 minutes;
iii) cooling to about 25° C. to obtain a precipitate; and
iv) filtering the precipitate to obtain the montelukast 1-methyl-3-phenylpropyl amine salt.

13. The process of claim 12, wherein the organic solvent is selected from the group consisting of $C_{1-4}$ alcohols, ketones, esters, ethers, aromatic hydrocarbons, cyclic hydrocarbons, water, and combinations thereof.

14. The process of claim 12, wherein the organic solvent is ethyl acetate, toluene, n-hexane, n-heptane, cyclohexane and mixtures thereof.

15. A process for preparing montelukast sodium comprising the steps of:

a) reacting 2-(2-(3(S)-(3-(2-(7-chloro-2-quinolinyl)-ethenyl)phenyl)-3-hydroxy propyl) phenyl)-2-propanol (diol compound) of formula

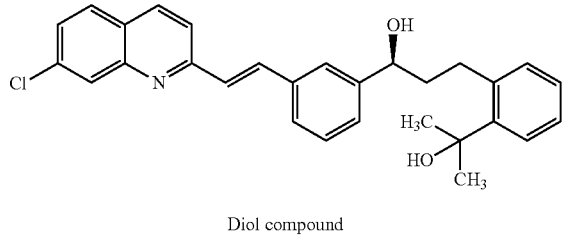 [SMILES: CC(C)(O)c1ccccc1CC[C@H](O)c1cccc(/C=C/c2ccc3ccc(Cl)cc3n2)c1]

Diol compound with methane sulfonyl chloride in an organic solvent in the presence of a base to obtain a solution of 2-(2-(3(S)-(3-(2-(7-chloro-2-quinolinyl)-ethenyl) phenyl)-3-methanesulfonyloxy propyl) phenyl)-2-propanol (mesylate compound)

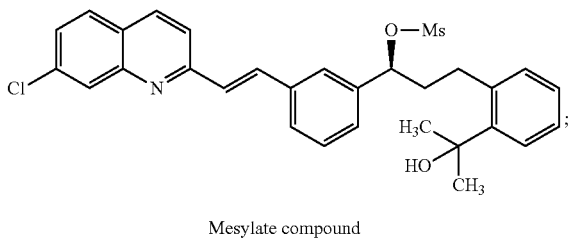 [SMILES: CC(C)(O)c1ccccc1CC[C@H](OS(C)(=O)=O)c1cccc(/C=C/c2ccc3ccc(Cl)cc3n2)c1]

Mesylate compound b) reacting 1-(mercaptomethyl)cyclopropane acetic acid

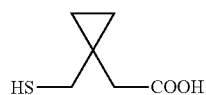

1-(mercaptomethyl)cyclopropane acetic acid with a base and an additional alkali source in a polar aprotic solvent to obtain a solution of dibase salt of 1-(mercaptomethyl)cyclopropane acetic acid;

c) reacting the mesylate compound of step a) with the dibase salt of 1-(mercaptomethyl)cyclopropane acetic acid of step b) at a temperature of about −20° C. to about 10° C. to obtain a montelukast intermediate;

d) converting the montelukast intermediate from step c) with 1-methy-3-phenylpropyl amine to obtain montelukast 1-methy-3-phenylpropyl amine salt;

e) neutralizing the montelukast 1-methy-3-phenylpropyl amine salt with an acid in a solvent to obtain montelukast;

f) treating the montelukast with an alcoholic sodium source; and g) isolating the montelukast sodium.

16. The process of claim 15, wherein the solvent in step e is selected from the group consisting of halogenated solvents and aromatic hydrocarbons.

17. The process of claim 15, wherein the solvent in step e is selected from the group consisting of dichloromethane, chloroform, dichloroethane, and toluene.

18. The process of claim 15, wherein the acid in step e is acetic acid.

19. The process of claim 15, wherein the alcoholic sodium source in step f is ethanolic sodium hydroxide.

* * * * *